US00RE50088E

(19) United States
(12) Reissued Patent
Shinoda

(10) Patent Number: US RE50,088 E
(45) Date of Reissued Patent: Aug. 20, 2024

(54) MICROCHIP FOR SORTING MICRO PARTICLES AND CARTRIDGE INCLUDING SAME

(71) Applicant: Sony Corporation, Tokyo (JP)

(72) Inventor: Masataka Shinoda, Tokyo (JP)

(73) Assignee: SONY CORPORATION, Tokyo (JP)

(21) Appl. No.: 17/514,186

(22) Filed: Nov. 12, 2021

Related U.S. Patent Documents

Reissue of:
(64) Patent No.: 9,588,036
Issued: Mar. 7, 2017
Appl. No.: 14/957,072
Filed: Dec. 2, 2015

U.S. Applications:
(63) Continuation of application No. 16/293,189, filed on Mar. 5, 2019, now Pat. No. Re. 48,827, which is an
(Continued)

(30) Foreign Application Priority Data

Feb. 17, 2009 (JP) ..... 2009-034337

(51) Int. Cl.
*G01N 15/1404* (2024.01)
*B01L 3/00* (2006.01)
(Continued)

(52) U.S. Cl.
CPC ..... *G01N 15/1404* (2013.01); *B01L 3/0268* (2013.01); *B01L 3/502761* (2013.01);
(Continued)

(58) Field of Classification Search
CPC ..... G01N 15/14; G01N 15/1404; G01N 15/1434; G01N 2015/1406;
(Continued)

(56) References Cited

U.S. PATENT DOCUMENTS 3,710,933 A 1/1973 Fulwyler et al.
5,061,361 A 10/1991 Gordon
(Continued)

FOREIGN PATENT DOCUMENTS

DE 202005008763 11/2006
EP 1872108 11/2008
(Continued)

OTHER PUBLICATIONS

Chinese Office Action issued Sep. 27, 2013 for corresponding Chinese Appln. No. 201080007366.1.
(Continued)

*Primary Examiner* — Carlos N Lopez
(74) *Attorney, Agent, or Firm* — K&L Gates LLP

(57) ABSTRACT

A microchip is provided that includes a flow path through which a liquid containing a micro particle flows, an orifice through which the liquid flowing through the flow path is discharged into a space outside the microchip, and a light-irradiated portion provided at a predetermined location of the flow path and configured to be irradiated with light. A width of the flow path and a depth of the flow path at the orifice are set to be smaller than a width of the flow path and a depth of the flow path at the light-irradiated portion, and the flow path is configured to gradually decrease from upstream of the orifice in a cross-section area perpendicular to a liquid-delivering direction between the light-irradiated portion and the orifice. A cartridge including the microchip is also provided.

23 Claims, 13 Drawing Sheets

Related U.S. Application Data application for the reissue of Pat. No. 9,588,036, which is a continuation of application No. 14/322,084, filed on Jul. 2, 2014, now Pat. No. 9,207,160, which is a continuation of application No. 13/147,517, filed as application No. PCT/JP2010/000775 on Feb. 9, 2010, now Pat. No. 8,795,500.

(51) Int. Cl.

| | |
|---|---|
| ***B01L 3/02*** | (2006.01) |
| ***G01N 15/14*** | (2006.01) |
| ***G01N 15/1434*** | (2024.01) |
| ***G01N 27/447*** | (2006.01) |
| *G01N 15/10* | (2006.01) |
| *G01N 15/1409* | (2024.01) |
| *G01N 15/149* | (2024.01) |

(52) U.S. Cl.

CPC .... *B01L 3/502776* (2013.01); *G01N 15/1434* (2013.01); *G01N 15/1459* (2013.01); *G01N 15/1484* (2013.01); *G01N 27/44743* (2013.01); *G01N 27/44791* (2013.01); *B01L 3/502746* (2013.01); *B01L 2400/0433* (2013.01); *B01L 2400/0487* (2013.01); *G01N 2015/1006* (2013.01); *G01N 2015/1028* (2024.01); *G01N 15/1409* (2024.01); *G01N 2015/1422* (2013.01); *G01N 2015/1481* (2013.01); *G01N 2015/1488* (2013.01); *G01N 15/149* (2024.01); *Y10T 137/8158* (2015.04)

(58) Field of Classification Search

CPC ... G01N 2015/1409; G01N 2015/1411; G01N 2015/1422; G01N 27/447; G01N 27/44756

See application file for complete search history.

(56) References Cited

U.S. PATENT DOCUMENTS

| | | | |
|---|---|---|---|
| 5,370,842 | A | 12/1994 | Miyazaki et al. |
| 6,263,745 | B1 | 7/2001 | Buchanan et al. |
| 6,281,018 | B1 | 8/2001 | Kirouac et al. |
| 8,266,950 | B2 | 9/2012 | Kaduchak et al. |
| 8,563,325 | B1 | 10/2013 | Bartsch et al. |
| 8,658,418 | B2 | 2/2014 | Daridon |
| 8,795,500 | B2 | 8/2014 | Shinoda |
| 9,207,160 | B2 * | 12/2015 | Shinoda ..... B01L 3/0268 |
| 2005/0068536 | A1 | 3/2005 | Schwabe |
| 2008/0286751 | A1 | 11/2008 | Renaud et al. |
| 2009/0122311 | A1 | 5/2009 | Kanda |
| 2009/0127167 | A1 | 5/2009 | Kirstein et al. |

FOREIGN PATENT DOCUMENTS

| | | |
|---|---|---|
| GB | 2383127 | 6/2003 |
| JP | HEI 03-122548 | 5/1991 |
| JP | HEI 05-240872 | 9/1993 |
| JP | 2003-107099 | 4/2003 |
| JP | 2003-287537 | 10/2003 |
| JP | 2005-513476 | 5/2005 |
| JP | 2007-046947 | 2/2007 |
| WO | 2005/042137 | 5/2005 |

OTHER PUBLICATIONS

Japanese Office Action issued Aug. 27, 2013 for corresponding Japanese Appln. No. 2009-034337.

Japanese Patent Office, Notification of reasons for refusal issued in connection with Japanese Patent Application No. 2009-034337, dated Oct. 2, 2012. (3 pages).

Ateya et al., "The good, the bad, and the tiny: a review of microflow cytometry", Anal. Bioanal. Chem., 2008, pp. 1485-1498, vol. 391.

Fu et al., "A microfabricated fluorescence-activated cell sorter", Nature Biotechnology, Nov. 1999, pp. 1109-1111, vol. 17.

European Search Report issued Jun. 19, 2012 for corresponding European Appln. No. 10743521.6.

International Search Report mailed Apr. 5, 2010, for corresponding Intl. Appln. No. PCT/JP2010/000775.

* cited by examiner

MICROCHIP FOR SORTING MICRO PARTICLES AND CARTRIDGE INCLUDING SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCES TO RELATED APPLICATIONS

The present application *is a continuation reissue application of Reissue application Ser. No. 16/293,189, filed on Mar. 5, 2019, now U.S. Patent Reissue Pat. No. RE48,827, which is an application for reissue of U.S. Pat. No. 9,588,036, filed as U.S. patent application Ser. No. 14/957,072 on Dec. 2, 2015, which* is a continuation of U.S. patent application Ser. No. 14/322,084, filed on Jul. 2, 2014, *now U.S. Pat. No. 9,207,160, issued on Dec. 8, 2015,* which is a continuation of U.S. patent application Ser. No. 13/147,517, filed on Aug. 2, 2011, now U.S. Pat. No. 8,795,500, *issued on Aug. 5, 2014,* which is a National Stage of International Application No. PCT/JP2010/000775 filed on Feb. 9, 2010, and which claims priority to Japanese Patent Application No. 2009-034337, filed on Feb. 17, 2009, the entire contents of which are incorporated herein by reference.

BACKGROUND

The present invention relates to an apparatus and a microchip for sorting micro particles. More specifically, the present invention relates to a micro-particle sorting apparatus and the like, that detects properties of micro particles, which flow through a flow path formed in a microchip, within the chip, discharges liquid drops containing the micro particles to the outside of the chip, and controls the movement directions of the liquid drops on the basis of the detected properties of the micro particles for sorting.

Conventionally, in order to identify properties of micro particles such as biologically-relevant micro particles such as cells, microorganisms, liposomes or synthetic particles such as latex particles, gel particles, or industrial particles, there has been utilized an apparatus that introduces dispersion liquid of the micro particles into the flow path, and optically measures the properties of the micro particles that have been introduced into the flow path.

In particular, regarding the biologically-relevant micro particles, there has been widely used an apparatus called a flow cytometry (flow cytometer) (see Non-Patent Document 1). As flow cytometries, there are those that are designed only for measurement of the properties of the micro particles, or those that are configured to be capable of sorting only the micro particles each having a predetermined property on the basis of the measurement result. Regarding the latter, particularly an apparatus for a cell being as a sorting target is called "cell sorter." The cell sorter currently available in the market is capable of measuring and sorting properties of cells at high speed, for example, several thousands to several tens thousands of cells per second.

In the conventional flow cytometry, properties of the size, the structure, and the like of the micro particles such as cells or micro beads are measured in the following manner. First, in a flow cell, sample solution containing micro particles being as measurement target is caused to flow into the center of a laminar flow of sheath liquid, to thereby arrange the micro particles in line in the flow cell. Next, in an optical detection portion, the micro particles arranged and flowing in the flow cell are irradiated with measurement light, and scattering light or fluorescence generating from the micro particles is detected. In this manner, the properties of the micro particles are measured. Subsequently, in a case where the sorting of the micro particles is performed, the sample liquid is discharged into a space outside the flow cell as liquid drops containing the micro particles, and movement directions of the liquid drops are controlled, to thereby sort the micro particles each containing a predetermined property.

Patent Document 1 (FIG. 7) discloses an apparatus, as the conventional cell sorter, which includes a fluid system for arranging cells stained with fluorescent labeling reagent or the like in line in the flow cell, and a sorting system for controlling the movement directions of the liquid drops discharged into the space outside the flow cell.

Each of those conventional flow cytometries (cell sorters) cannot be easily disposed of by a user because the flow cell part constituting the flow path system is made of expensive quartz and is constituted of the orifice part separate from the flow cell. Thus, even if the flow cell part and the orifice part are sufficiently washed in every measurement, there is a fear that cross contamination of samples between measurements occur. Further, the space constituting the sorting system is set as an open space or a space having low air tightness, and hence contamination materials such as micro liquid drops (aerosol) generating during formation of the liquid drops may be mixed into a sample at the time of measurement, or biohazard such as infection or exposure with respect to apparatus users due to the aerosol may occur. The cross contamination between the samples, the contamination of the sample, the biohazard with respect to the users, and the use of the flow cell and the orifice part, which are expensive, as described above remain obstacles particularly in a case of using stem cells or the like, which have been sorted by the cell sorter, for regenerative medicine.

As a technique for addressing the cross contamination between the samples, the contamination of the sample, the biohazard with respect to the users, and the use of the flow cell and the orifice part, which are expensive, there has been, in recent years, developed a microchip including a silicon or glass substrate on which an area for performing a chemical and biological analysis and a flow path are provided. The analysis system using such a microchip is called μ-TAS (micro-total-analysis system), lab-on-a-chip, biochip, or the like.

As an example of applying the μ-TAS to the micro-particle sorting technique, there is a micro-particle sorting technique of optically, electrically, or magnetically analyzing the properties of the micro particles in the flow path or the area provided on the microchip. For example, Patent Document 2 discloses a micro-particle classifying microchip including, on a substrate, a micro-particle-containing solution introducing flow path, a sheath flow forming flow path arranged in at least one side portion of that flow path, a micro-particle measuring location for measuring the introduced micro particles, and two or more micro-particle classifying flow paths for classifying and collecting the micro particles, which are placed downstream with respect to the micro-particle measuring location. This microchip includes electrodes near the opening of the flow path from the micro-particle measuring location to the micro-particle classifying flow paths. According to the micro-particle sorting apparatus including this microchip, it is possible to control the movement directions of the micro particles due to interaction with respect to the electric field of the electrodes, to thereby sort the micro particles.

In the flow cytometry (cell sorter) applying the μ-TAS, the microchip enabling a disposable use (which is disposable) can constitute the flow path system. Therefore, the cross contamination of the samples between measurements does not occur. Further, the sorting system can be arranged in the airtight flow path provided in the chip. Therefore, no contamination material such as the aerosol is mixed into the sample during measurement. However, it is necessary to deliver at high pressure the liquid containing the micro particles through the flow path provided in the chip. Further, it is necessary to perform the control of the movement directions of the micro particles in such a state that the micro particles are flowing in the liquid. Therefore, it is difficult to increase the flowing velocity of the micro particles and the sorting speed, and to measure and sort the properties of the cells at high speed, for example, several thousands to several tens thousands of cells per second as in the conventional flow cytometry (cell sorter).

CITED DOCUMENT

Patent Document

Patent Document 1: Japanese Patent Application Laid-open No. 2007-46947

Patent Document 2: Japanese Patent Application Laid-open No. 2003-107099

Non-Patent Document

Non-Patent Document 1: Hiromitsu Nakauchi: Supplementary Volume of Cell Technology, Experimental Protocol Series, Master of Flow Cytometry, Shujunsha, second edition, published at 31 Aug. 2006

SUMMARY

Problem to be Solved by the Invention

As described above, in the conventional flow cytometry (cell sorter), the flow cell constituting the flow path system is not configured to be disposable, and hence there is a fear that cross contamination between samples occurs. Further, the space constituting the sorting system is set as an open space or a space having low air tightness, and hence the sample may be contaminated by the aerosol or the like. Further, even in the flow cytometry (cell sorter) applying the μ-TAS, it is difficult to increase the flowing velocity of the micro particles and the sorting speed, and hence there is a problem that it is difficult to achieve a high-throughput analysis.

In view of this, it is a main object of the present invention to provide a micro-particle sorting apparatus capable of performing a high-speed analysis and a safe, high-speed, inexpensive sorting by eliminating the cross contamination between the samples, the contamination of the sample, biohazard with respect to the users, and the use of the flow cell and the orifice part, which are expensive.

Means for Solving the Problem

In order to solve the above-mentioned problems, the present invention provides a micro-particle sorting apparatus including: a microchip in which a flow path through which liquid containing a micro particle flows and an orifice through which the liquid flowing through the flow path is discharged as a liquid drop into a space outside the chip are provided; an oscillating element for transforming the liquid into the liquid drop and discharging the liquid drop at the orifice; a charge means for adding an electric charge to the discharged liquid drop; an optical detection means that detects an optical property of the micro particle flowing through the flow path, upstream of a liquid-delivering direction with respect to the orifice; paired electrodes provided so as to be opposed to each other while sandwiching the moving liquid drop therebetween along a movement direction of the liquid drop discharged into the space outside the chip; and two or more containers that collect the liquid drop passing between the paired electrodes, in which a width of the flow path and a depth of the flow path at a location of the orifice are set to be smaller than a width of the flow path and a depth of the flow path at a location at which the optical property of the micro particle is detected by the optical detection means, or in which a cross-section area of the flow path at a location of the orifice is set to be smaller than a cross-section area of the flow path at a location at which the optical property of the micro particle is detected by the optical detection means.

This micro-particle sorting apparatus may include a micro tube that introduces, into a laminar flow of liquid T flowing through the flow path, a laminar flow of another liquid S containing the micro particle, upstream of the liquid-delivering direction with respect to the location at which the optical property of the micro particles is detected by the optical detection means.

Further, this micro tube can be configured as the charge means by forming the micro tube of a metal on which voltage can be applied.

In this micro-particle sorting apparatus, it is preferred that at least the orifice portion of the microchip and the space in which the liquid drop discharged outside through the orifice moves be arranged in a cavity of the cartridge having light transmittance for light from the optical detection means.

In addition, it is preferred that the cavity of this cartridge be configured to be hermetically sealed.

The present invention further provides a microchip, in which a flow path through which liquid containing a micro particle flows and an orifice through which the liquid flowing through the flow path is discharged into a space outside the chip are provided, a predetermined location of the flow path is configured as a light-irradiated portion to be irradiated with light from an optical detection means for detecting an optical property of the micro particle flowing therethrough, a micro tube that introduces, into a laminar flow of liquid T flowing through the flow path, a laminar flow of another liquid S containing micro particle, upstream of the liquid-delivering direction with respect to the light-irradiated portion is provided, and a width of the flow path and a depth of the flow path at a location of the orifice are set to be smaller than a width of the flow path and a depth of the flow path at the light-irradiated portion, or a cross-section area of the flow path at a location of the orifice is set to be smaller than a cross-section area of the flow path at the light-irradiated portion.

This microchip may include an oscillating element for transforming the liquid into a liquid drop and discharging the liquid drop at the orifice.

In the microchip, it is preferred that the micro tube be formed of a metal on which voltage can be applied.

The present invention further provides a cartridge which has a cavity in which at least the orifice portion of the microchip according to claim 10 and the space in which the liquid drop discharged outside through the orifice moves are configured, and has light transmittance with which light from the optical detection means is caused to transmit to the light-irradiated portion.

It is preferred that the cavity of this cartridge be configured to be hermetically sealed.

Effects of the Invention

According to the present invention, it is possible to provide the micro-particle sorting apparatus capable of performing the high-speed analysis and the safe, high-speed, inexpensive sorting by eliminating the cross contamination between the samples, the contamination of the sample, the biohazard with respect to the users, and the use of the flow cell and the orifice part, which are expensive.

Additional features and advantages are described herein, and will be apparent from the following Detailed Description and the figures.

BRIEF DESCRIPTION OF THE FIGURES

FIG. 7A shows a cross-section of the flow path 11 at an opening position of the micro tube 16, FIG. 7B shows a cross-section of the flow path 11 at a light-irradiated portion 33, FIG. 7C shows a cross-section of the flow path 11 at a location of the orifice 12.

DETAILED DESCRIPTION

Hereinafter, a preferred mode for carrying out the invention will be described with reference to the drawings. It should be noted that an embodiment to be described below shows one example of a typical embodiment of the present invention, and shall not be construed to limit the scope of the present invention. It should be noted that the description will be made in the following order.

Figure 1:
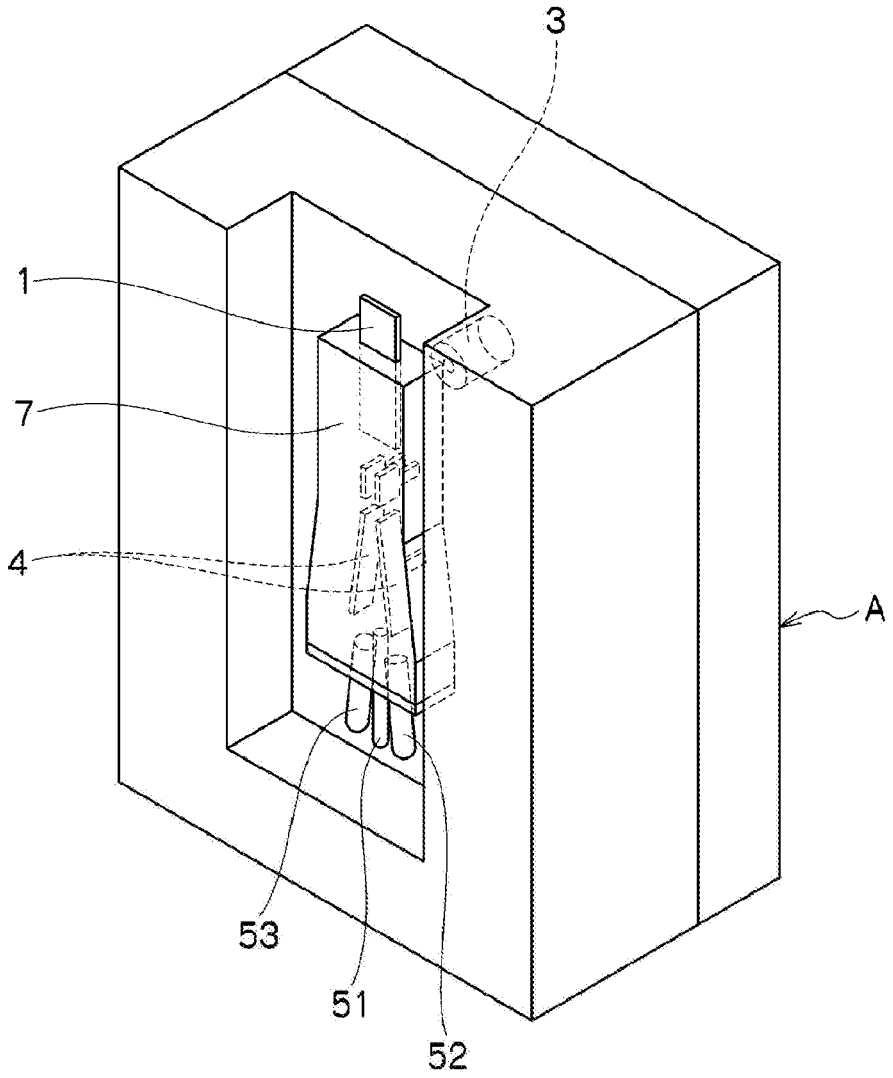
FIG. 1 A view showing a schematic configuration of a micro-particle sorting apparatus A according to the present invention.

1. Micro-particle sorting apparatus
2. Microchip
(1) Flow path
(2) Micro tube and limiter portion
(3) Light-irradiated portion
(4) Pressure-rising portion and orifice
3. Oscillating element
4. Width and Depth of flow path at each location of microchip
5. Operation of micro-particle sorting apparatus
6. Cartridge 1. Micro-Particle Sorting Apparatus FIG. 1 is a view showing a schematic configuration of a micro-particle sorting apparatus according to the present invention. In the drawing, the micro-particle sorting apparatus denoted by the symbol A is mainly constituted of a cartridge 7 including a microchip 1 *or micro fluidic structure* as a component and of an apparatus main body including an optical detection means 3 that radiates the light to a predetermined location of the microchip 1 *or micro fluidic structure*. The microchip 1 is in such a state that one part thereof is exposed to the outside of the cartridge and the other part is housed within the cartridge 7. In the inside of the cartridge 7, a pair of paired electrodes 4, 4 are provided. Further, to a side in opposite to the microchip 1, of the cartridge 7, three containers (numerals 51, 52, 53) are connected so that the inside of each container is in communication with the cavity of the cartridge. The cartridge 7 includes the microchip 1, the paired electrodes 4, 4, and the containers 51 to 53 as components is detachably attached to the main body of the micro-particle sorting apparatus A. In the main body of the micro-particle sorting apparatus A, during attachment of the cartridge 7, an oscillating element (not shown) is provided at a position at which it is brought into contact with a part of the microchip 1 *or micro fluidic structure*.

Figure 2:
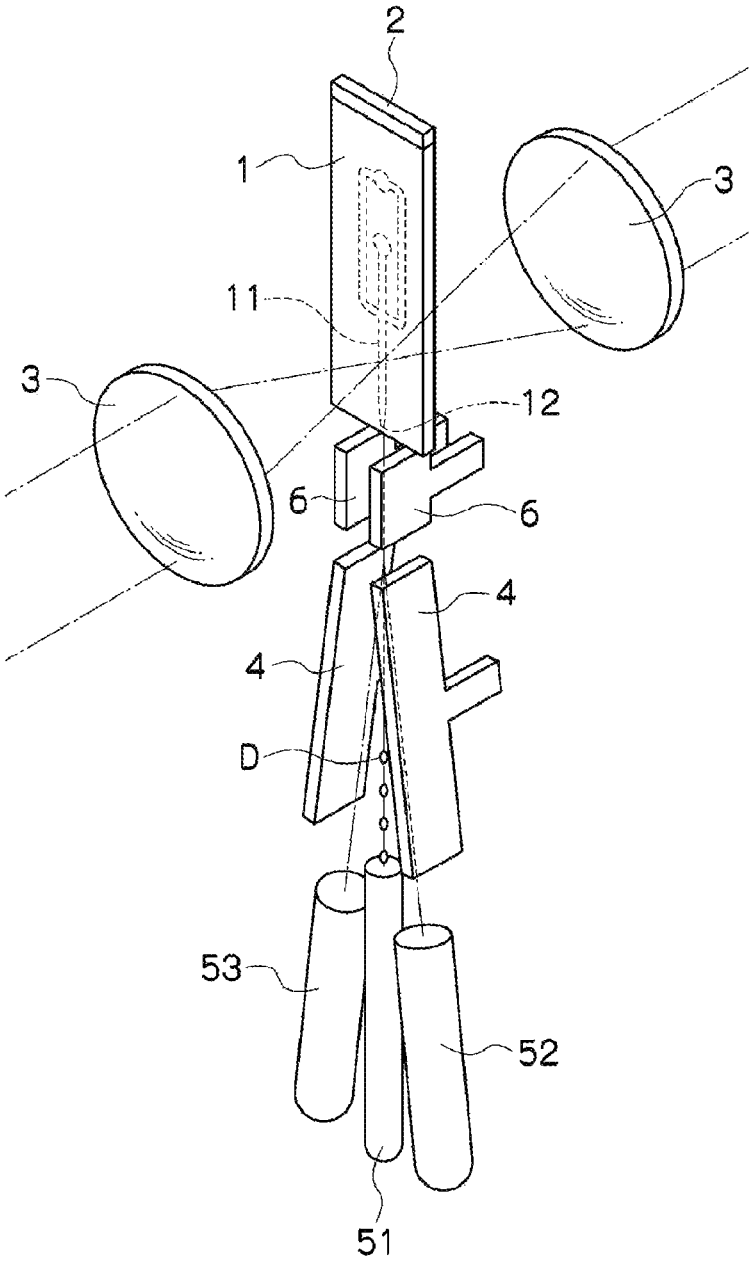
FIG. 2 A view showing a schematic configuration of the micro-particle sorting apparatus A.

A configuration of the micro-particle sorting apparatus A will be described in detail with reference to FIG. 2. FIG. 2 is a view showing the schematic configuration of the micro-particle sorting apparatus A. The drawing shows the microchip 1 and the optical detection means 3, the paired electrodes 4, 4, and the containers 51 to 53 which are described above. In the drawing, the numeral 2 denotes the oscillating element provided so as to be brought into contact with the part of the microchip 1 during attachment of the cartridge 7 to the main body of the micro-particle sorting apparatus A. Further, the numerals 6, 6 denote grounding paired electrodes that have been grounded. It should be noted that here, the illustration of the cartridge 7 is omitted.

In the microchip 1, there is formed a flow path 11 through which liquid (sample liquid) containing micro particles being as sorting targets flows. The optical detection means 3 radiates light (measurement light) to a predetermined location of the flow path 11, and detects light (measurement target light) generating from the micro particles flowing through the flow path 11. Hereinafter, in the flow path 11, the location to be irradiated with the measurement light from the optical detection means 3 is referred to as a "light-irradiated portion."

The microchip 1 can be formed of glass or various type of plastics (PP, PC, COP, PDMS, for example). The material of the microchip is desirably material having transmittance for the measurement light radiated from the optical detection means 3 and low autofluorescence and causing small optical error due to its small wavelength dispersion.

Formation of the flow path 11 in the microchip 1 *or micro fluidic structure* can be performed by wet etching or dry etching with respect to a glass substrate, or by nano-imprinting, injection molding, or machining with respect to a plastic substrate. The microchip 1 can be formed by sealing a substrate, on which the flow path 11 and the like have been formed, with a substrate made of the same material or a different material.

The optical detection means 3 can be configured similarly to the conventional flow cytometry. Specifically, the optical detection means 3 is constituted of a laser light source, an irradiation system, and a detection system. The irradiation system is composed of collecting lens, a dichroic mirror, a bandpass filter, and the like for collecting and radiating the laser light with respect to the micro particles. The detection system detects the measurement target light generating from the micro particles due to the irradiation of the laser light. The detection system is, for example, constituted of a PMT (photo multiplier tube) and an area-image pick-up element such as a CCD or CMOS element. It should be noted that although FIG. 2 shows the case where the irradiation system and the detection system are individually configured, the irradiation system and the detection system are configured through the same optical path (see FIG. 1).

The measurement target light to be detected by the detection system of the optical detection means 3 is light generating from the micro particles due to the irradiation of the measurement light. The measurement target light can be, for example, forward scatter or side scatter, scattering light including Rayleigh scattering or Mie scattering, or fluorescence. The measurement target light is converted into an electrical signal, and optical properties of the micro particles are detected according to this electrical signal.

The sample liquid passing through the light-irradiated portion is discharged through an orifice provided at one end of the flow path 11 into the space outside the chip. At this time, the oscillating element 2 oscillates the microchip 1 so that the sample liquid can be transformed into liquid drops, and the liquid drops are discharged into the space outside the chip. In FIG. 2, the symbol D denotes the liquid drops discharged into the space outside the chip.

The liquid drops D can contain the micro particles being as the sorting targets. The paired electrodes 4, 4 are provided along movement direction of the liquid drop discharged into the space outside the chip, and arranged so as to be opposed to each other while sandwiching each of the moving liquid drops therebetween. To the discharged liquid drop, an electric charge is added by a charge means (not shown). The paired electrodes 4, 4 controls, with its electrical repelling force (or attracting force) with respect to the electric charge added to the liquid drop, the movement direction of the liquid drop. In this manner, the liquid drop is guided into any one of the containers 51 to 53. It should be noted that the containers 52 and 53 that collect the liquid drops may be a commonly-used plastic test-tube container as shown in the drawing or the like, or may be a sorting plate container including a plastic substrate on which 96 wells and the like are formed or the like.

As described above, the micro-particle sorting apparatus A is characterized in that processes up to the property detection of the micro particles by the optical detection means 3 are performed in the microchip 1, and then, the control of the movement directions of the micro particles is performed in the space outside the chip. In the micro-particle sorting apparatus A, on the basis of the optical properties of the micro particles, which are detected by the optical detection means 3, the movement directions of the liquid drops each containing the micro particle are controlled by the paired electrodes 4, 4, and hence the micro particles each having a desired property can be collected by any one of the containers 51 to 53 for sorting.

It should be noted that in the micro-particle sorting apparatus A, the optical detection means 3 may be replaced, for example, by an electrical or magnetic detection means. In a case of electrically or magnetically detecting the properties of the micro particles, on both sides of the flow path 11, micro electrodes are provided so as to be opposed to each other in order to measure resistance, capacitance, inductance, impedance, and value of change in electrical field between the electrodes, or magnetization, a change in magnetic field, and the like. In this case, the sorting of the micro particles is performed on the basis of electrical or magnetic properties of the micro particles.

Hereinafter, details of the respective components of the micro-particle sorting apparatus A and functions thereof will be described in order. First, with reference to FIGS. 3 to 8, the microchip 1 and the oscillating element 2 will be described.

2. Microchip (1) Flow Path

Figure 3:
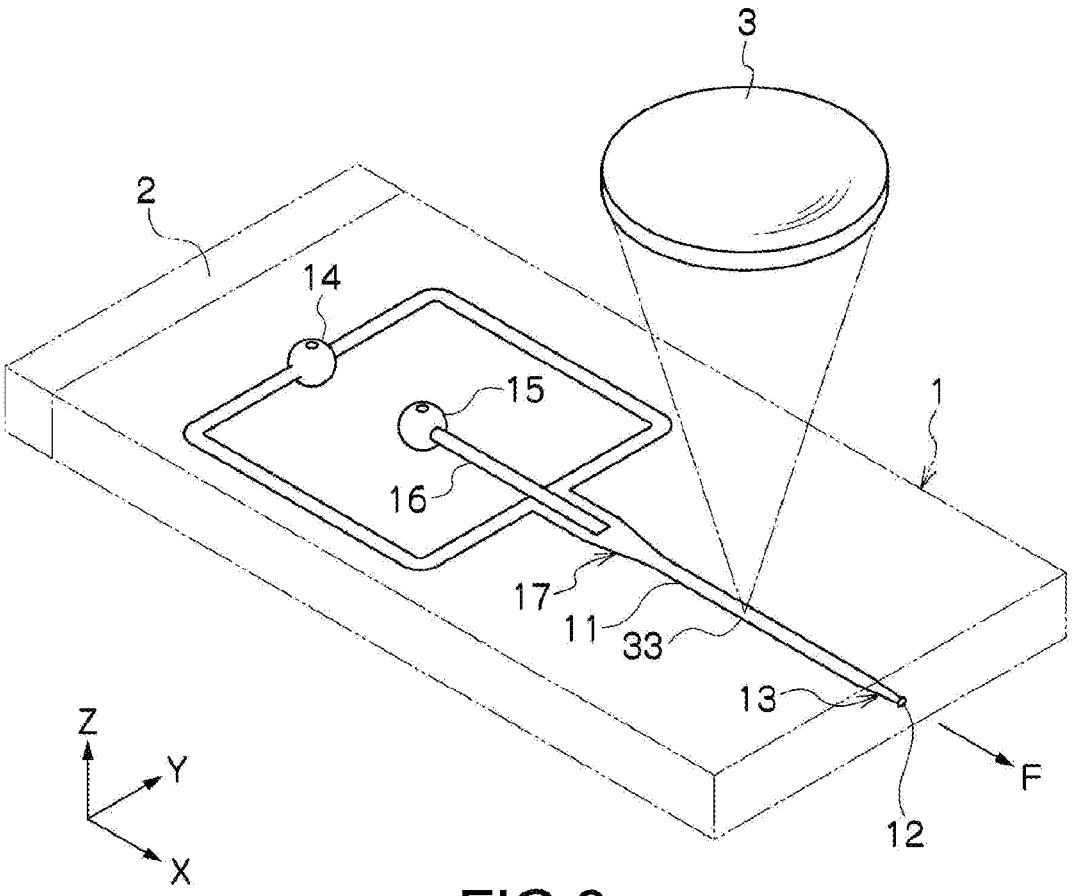
FIG. 3 A view showing schematic configurations of a microchip 1 and an oscillating element 2.

FIG. 3 is a view showing schematic configurations of the microchip 1 and the oscillating element 2. In the microchip 1, a sample inlet 15 through which the sample liquid is introduced, and a sheath liquid inlet 14 through which sheath liquid is introduced are formed. The sheath liquid introduced into the sheath liquid inlet 14 branches into two directions of the Y-axis positive and negative directions and is delivered through the flow path 11, caused to turn at approximately 90 degrees twice before convergence, and then delivered to the downstream.

(2) Micro Tube and Limiter Portion

At the location of the flow path 11, at which the sheath liquid is converged, a micro tube 16 for introducing the sample liquid, which has been introduced from the sample inlet 15, into a sheath-liquid laminar flow is provided. A sample-liquid laminar flow passes through the micro tube 16 and is introduced into the sheath-liquid laminar flow that is introduced from the sheath liquid inlet 14 and passes through the flow path 11. With this, the sample-liquid laminar flow can be delivered to the downstream of the flow path 11 while being surrounded with the sheath-liquid laminar flow.

The micro tube 16 is formed of a metal on which voltage can be applied, and is configured as the charge means that adds a positive or negative charge with respect to the sheath liquid and the sample liquid flowing through the flow path 11. The sample liquid and the sheath liquid are transformed into liquid drops through the orifice 12 provided at one end of the flow path 11, and the liquid drops are discharged into the space outside the chip. At this time, by applying on the micro tube 16 voltage, it is possible to add the positive or negative charge to the liquid drop to be discharged.

In FIG. 3, the numeral 17 denotes a limiter portion provided to the flow path 11. The limiter portion 17 is formed so as to have a cross-section perpendicular to a liquid-delivering direction, which gradually decreases in area from the upstream to the downstream of the flow path.

Figure 4:
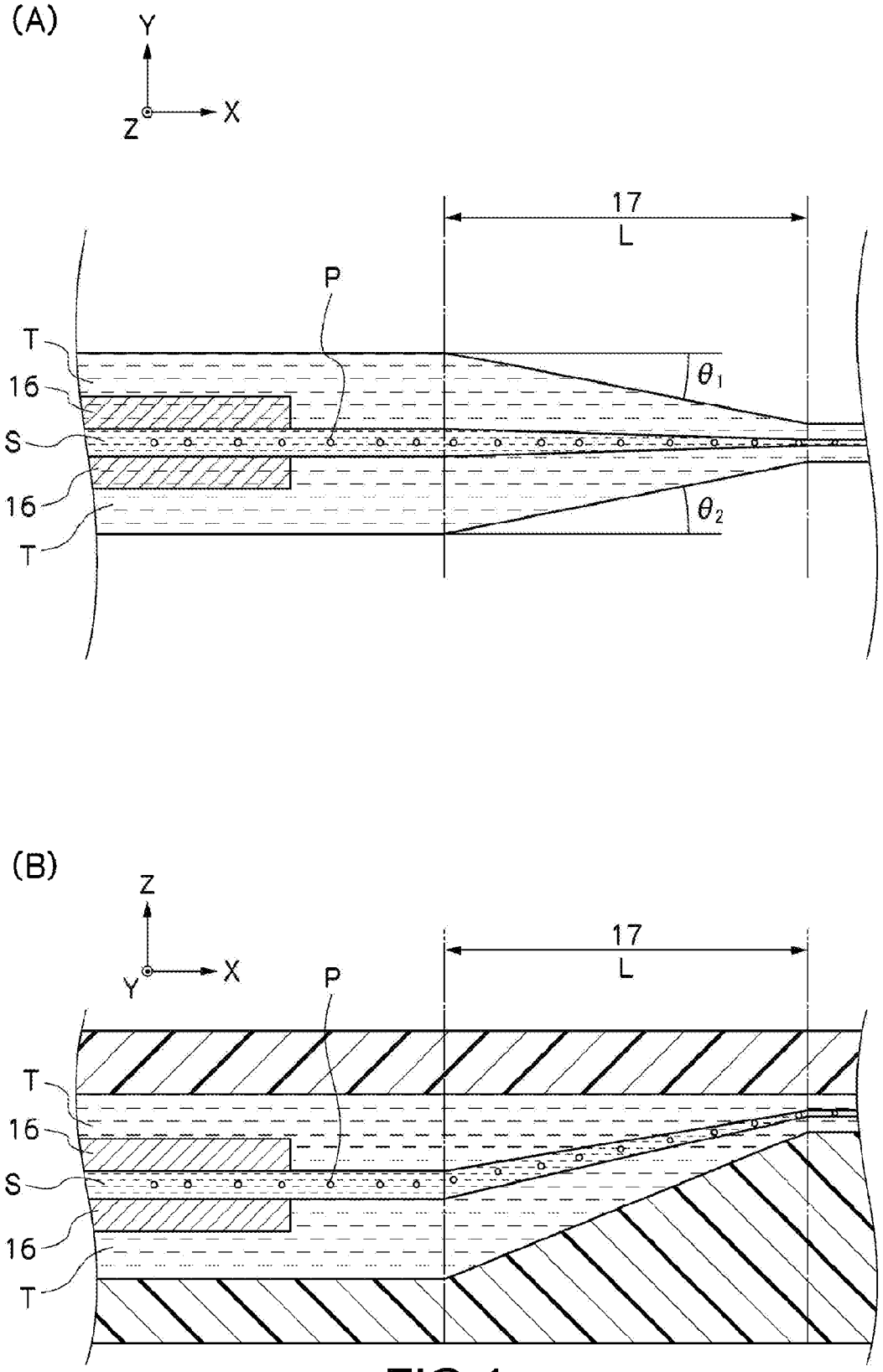
FIG. 4 Sectional schematic views describing a *micro fluidic* structure of a flow path 11 in vicinity of a provision location of a micro tube 16 and a limiter portion 17, and a state of a sample-liquid laminar flow and a sheath-liquid laminar flow, which pass therethrough.

FIG. 4 are sectional schematic views describing a *micro fluidic* structure of the flow path 11 in vicinity of the provision location of the micro tube 16 and the limiter portion 17 and a state of the sample-liquid laminar flow and the sheath-liquid laminar flow, which pass therethrough.

FIG. 4A shows a horizontal sectional view (XY sectional view), and FIG. 4B shows a vertical sectional view (ZX sectional view). In the drawing, the symbol S denotes the sample-liquid laminar flow, the symbol T denotes the sheath-liquid laminar flow, and the symbol P denotes the sorting-target micro particles contained in the sample liquid.

The sample-liquid laminar flow S is introduced through the micro tube 16 into the sheath-liquid laminar flow T passing through the flow path 11, and then, delivered in such a state that the sample-liquid laminar flow S is surrounded with the sheath-liquid laminar flow T as shown in the drawing (as three-dimensional laminar flow).

Sidewalls of the flow path at the limiter portion 17 are formed so that the space therebetween narrows in the Y-axis direction in the drawing along the liquid-delivering direction. The limiter portion 17 has a counterbalance shape, which becomes gradually slimmer as viewed from above. With this shape, the limiter portion 17 limits the width of the laminar flow of the sheath liquid and the sample-liquid in the Y-axis direction in the drawing and delivers the laminar flow of the sheath liquid and the sample-liquid. Further, the limiter portion 17 is formed so that a bottom surface of the flow-path thereof is an inclined surface increasing in height in a depth direction (Z-axis positive direction) from the upstream to the downstream. The limiter portion 17 limits also the width of the laminar flow in that direction.

As described above, when the sample-liquid laminar flow S forms the three-dimensional laminar flow, surrounded with the sheath-liquid laminar flow T, and this three-dimensional laminar flow is delivered with the width of the laminar flow of the three-dimensional laminar flow being limited, the sheath-liquid laminar flow T can be delivered in such a state that the micro particles P are arranged in line in the limited sample-liquid laminar flow S. Further, it is possible to determine a flowing position of the micro particle P in the flow path 11, and to accurately radiate the measurement light from the optical detection means 3 to the micro particles P.

In particular, the limiter portion 17 can limit the width of the laminar flow of the sample-liquid laminar flow S not only in the horizontal direction of the microchip 1 (Y-axis direction of FIG. 4A), but also the vertical direction (Z-axis direction of FIG. 4B). Thus, a focus position of the measurement light in the depth direction of the flow path 11 can be caused to precisely correspond to the flowing position of the micro particle P. Therefore, it is possible to accurately radiate the measurement light to the micro particles P and to obtain a high measurement sensitivity.

Here, it is conceivable that if the flow path 11 is formed as a sufficiently slim flow path, and a micro tube 16 having a small diameter is used to introduce the sample-liquid laminar flow S into the sheath-liquid laminar flow T passing through the flow path 11, it is also possible to form the three-dimensional laminar flow having a previously limited laminar flow width. However, in this case, due to the small diameter of the micro tube 16, the micro tube 16 may get blocked by the micro particles P.

In the microchip 1, the limiter portion 17 is provided, and hence using the micro tube 16 having a diameter sufficiently larger than the diameter of each micro particle P contained in the sample liquid, the three-dimensional laminar flow is formed, the width of the laminar flow can be limited. Therefore, the problem of blocking of the micro tube 16 as described above does not occur.

FIG. 4 show a case where the micro tube 16 is provided so that its center is coaxially positioned with respect to the center of the flow path 11. In this case, the sample-liquid laminar flow S is introduced into the center of the sheath-liquid laminar flow T passing through the flow path 11. The position of the sample-liquid laminar flow S in the sheath-liquid laminar flow T can be arbitrarily set by adjusting an opening position of the micro tube 16 in the flow path 11. Further, for limitation of the width of the laminar flow, it is sufficient that the limiter portion 17 be formed so as to have the cross-section perpendicular to the liquid-delivering direction, which gradually decreases in area from the upstream to the downstream of the flow path. The shape of the limiter portion 17 be not limited to the shape shown in FIG. 4, and, for example, the limiter portion 17 may be formed so that both of the bottom surface of the flow-path and the top surface of the flow-path are as inclined surfaces in order to perform the limitation.

The inner diameter of the micro tube 16 can be appropriately set depending on the diameter of each micro particle P being as the sorting target. For example, in a case where blood is used as the sample liquid and cells in the blood are analyzed, it is preferred that the inner diameter of the micro tube 16 range from approximately 10 to 500 μm. Further, it is sufficient that the width and the depth of the flow path 11 at the opening position of the micro tube 16 be appropriately set depending on the outer diameter of the micro tube 16 reflecting the diameter of each micro particle P. For example, in a case where the inner diameter of the micro tube 16 ranges from approximately 10 to 500 μm, it is preferred that each of the width and the depth of the flow path 11 at the opening position of the micro tube 16 range from approximately 100 to 2000 μm. It should be noted that the shape of the cross-section of the micro tube can be an appropriate shape such as an oval shape, a quadrangle, or a triangular shape other than the circular shape.

Although the width of the laminar flow of the sample-liquid laminar flow S and the sheath-liquid laminar flow T before limitation by the limiter portion 17 can vary depending on the width and the depth of the flow path 11 and the diameter of the micro tube 16, it is possible to limit the width of the laminar flow into an appropriate laminar flow width by appropriately adjusting the area of the cross-section of the limiter portion 17, the cross-section being perpendicular to the liquid-delivering direction. For example, in FIG. 4B, when a length of the flow path at the limiter portion 17 is denoted by L and an angle of inclination of the bottom surface of the flow-path is denoted by θ3, a limitation width of the three-dimensional laminar flow at the limiter portion 17 is L*tan θ3. Therefore, by appropriately adjusting the length of the flow path L and the angle of inclination θ3, an appropriate limitation width can be set. In addition, in FIG. 4A, when narrowing angles in the Y-axis direction of sidewalls of the flow path at the limiter portion 17 are denoted by θ1, θ2, respectively, and these angles and the above-mentioned θ3 are set to "θ3=2×θ1, θ1=θ2," the sample-liquid laminar flow S and the sheath-liquid laminar flow T can be isotropically reduced in size. Thus, it is possible to limit the width of the laminar flow without disturbing the three-dimensional laminar flow formed through the micro tube 16.

(3) Light-Irradiated Portion

In FIG. 3, the numeral 33 denotes the light-irradiated portion to be irradiated with the measurement light from the optical detection means 3. In the light-irradiated portion 33, the measurement target light generating from each of the micro particles due to the irradiation of the measurement light from the optical detection means 3 is detected.

As previously mentioned, in the light-irradiated portion 33, the limiter portion 17 limits the width of the laminar flow of the sample-liquid laminar flow and the sheath-liquid laminar flow. Therefore, it is possible to cause the focus position of the measurement light to precisely correspond to the flowing position of the sample-liquid laminar flow S in the flow path 11, so that the micro particle can be accurately irradiated with the measurement light.

The laminar flow width of the sample-liquid laminar flow S and the sheath-liquid laminar flow T at the light-irradiated portion 33 can be set to be an appropriate laminar flow width by appropriately adjusting the area of the cross-section of the limiter portion 17, the cross-section being perpendicular to the liquid-delivering direction. Preferably, each of the width and the depth of the flow path 11 ranges from approximately 20 to 2000 μm.

(4) Pressure-Rising Portion and Orifice

In FIG. 3, the numeral 12 denotes the orifice for discharging the sheath liquid and the sample liquid, which have passed through the light-irradiated portion 33, into the space outside the chip. The sheath liquid and the sample liquid are transformed into liquid drops through the orifice 12 due to action of the oscillating element 2 to be described below and the liquid drops are discharged into the outside of the chip.

The numeral 13 denotes a pressure-rising portion provided upstream with respect to the orifice 12 and downstream with respect to the light-irradiated portion 33 in the flow path 11. The pressure-rising portion 13 is formed so as to have the cross-section perpendicular to the liquid-delivering direction, which gradually decreases in area from the upstream to the downstream of the flow path. That is, similarly to the limiter portion 17, sidewalls of the flow path are formed so that the space therebetween narrows in the Y-axis direction in the drawing along the liquid-delivering direction. Further, the pressure-rising portion 13 is formed so that a bottom surface of the flow-path thereof is an inclined surface increasing in height from the upstream to the downstream in a depth direction (Z-axis positive direction).

Figure 5:
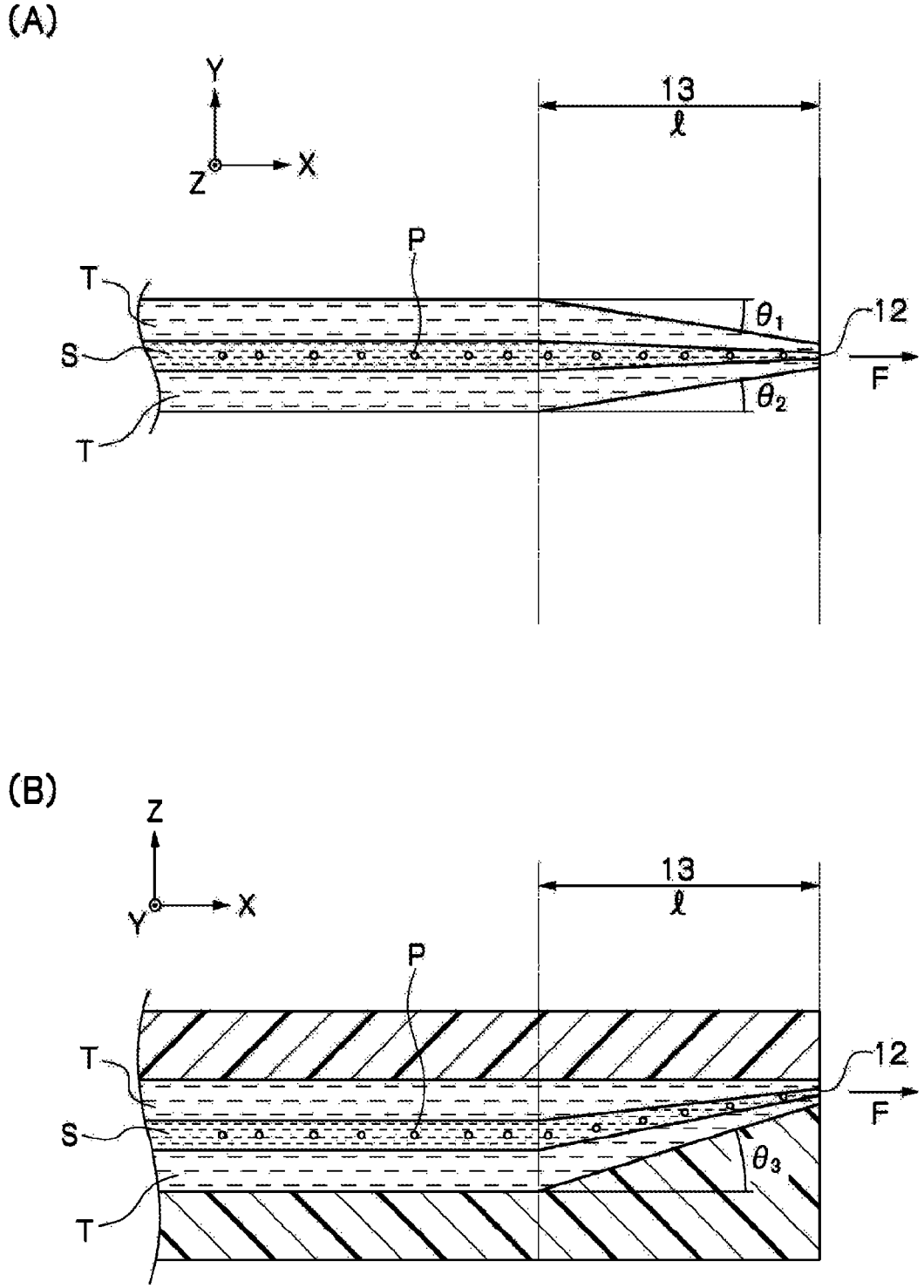
FIG. 5 Sectional schematic views describing a *micro fluidic* structure of the flow path 11 in vicinity of a pressure-rising portion 13 and an orifice 12, and the sample-liquid laminar flow and the sheath-liquid laminar flow, which pass therethrough.

FIG. 5 are sectional schematic views describing a *micro fluidic* structure of the flow path 11 in vicinity of the pressure-rising portion 13 and the orifice 12, and a state of the sample-liquid laminar flow and the sheath-liquid laminar flow, which pass therethrough. FIG. 5A shows a horizontal sectional view (XY sectional view), and FIG. 5B shows a vertical sectional view (ZX sectional view). In the drawing, the symbol S denotes the sample-liquid laminar flow, the symbol T denotes the sheath-liquid laminar flow, and the symbol P denotes the sorting-target micro particles contained in the sample liquid.

The sample-liquid laminar flow S and the sheath-liquid laminar flow T are delivered in such a state that the width of the laminar flow is limited in the Y-axis direction and the Z-axis direction in the drawing at the pressure-rising portion 13. Due to this limitation of the width of the laminar flow, the pressure-rising portion 13 functions to increase a liquid-delivering pressure of the sample liquid and the sheath liquid in the flow path 11, to thereby discharge them at high pressure through the orifice 12. This function of the pressure-rising portion 13 allows, during transformation into liquid drops through the orifice 12, the liquid drops to be formed at higher frequency. Thus, high speed sorting can be realized. In FIGS. 3 and 5, a movement direction of the discharged liquid drops is denoted by the symbol F.

The laminar flow width of the sample-liquid laminar flow S and the sheath-liquid laminar flow T at the location of the orifice 12 can be limited to an appropriate laminar flow width by appropriately adjusting the area of the cross-section of the pressure-rising portion 13, the cross-section being perpendicular to the liquid-delivering direction. For example, in FIG. 5B, when the length of the flow path at the pressure-rising portion 13 is denoted by 1, and the angle of inclination of the bottom surface of the flow-path is denoted by θ3, the limitation width of the three-dimensional laminar flow at the pressure-rising portion 13 is L*tan θ3. Therefore, by appropriately adjusting the length of the flow path 1 and the angle of inclination θ3, an appropriate limitation width can be set. It is preferred that regarding the width of the laminar flow of the sample-liquid laminar flow S and the sheath-liquid laminar flow T at the location of the orifice 12, each of the width and the depth at the location of the orifice 12 range from approximately 20 to 500 μm.

It should be noted that limitation of the width of the laminar flow of the sample-liquid laminar flow S and the sheath-liquid laminar flow T may be performed in such a manner that both of the bottom surface of the flow-path and the top surface of the flow-path at the pressure-rising portion 13 is set as inclined surfaces, and the shape of the pressure-rising portion 13 is not limited to the shape shown in the drawing. These points are the same as in the case of the limiter portion 17. Further, in FIG. 5A, when narrowing angles in the Y-axis direction of sidewalls of the flow path at the pressure-rising portion 13 are denoted by θ1, θ2, respectively, and the narrowing angle θ3 in the Z-axis direction are set to "θ3=2×θ1, θ1=θ2," the three-dimensional laminar flow formed through the micro tube 16 can be isotropically reduced in size. Thus, it is possible to limit the width of the laminar flow without disturbing the three-dimensional laminar flow formed through the micro tube 16. This point is also the same as described above with respect to the limiter portion 17.

3. Oscillating Element

In FIG. 3, the numeral 2 denotes the oscillating element that is brought into contact with the part of the microchip 1 during attachment of the cartridge 7 to the main body of the micro-particle sorting apparatus A (see FIG. 1). Here, a case of providing the oscillating element 2 on the main body side of the micro-particle sorting apparatus A will be described. However, the oscillating element 2 may be provided integrally with the chip as an inner component of the microchip 1.

The oscillating element 2 oscillates the microchip 1 at a predetermined frequency, to thereby transform the sample liquid and the sheath liquid into liquid drops and discharge the liquid drops at the orifice 12. The transformation into liquid drops of the sample liquid and the sheath liquid using the oscillating element as described above can be performed in the same manner as that of the conventional a flow cytometry using flow cell. The oscillating element 2 is constituted of, for example, a piezo oscillating element also adopted in an ink-jet printer or the like.

Figure 6:
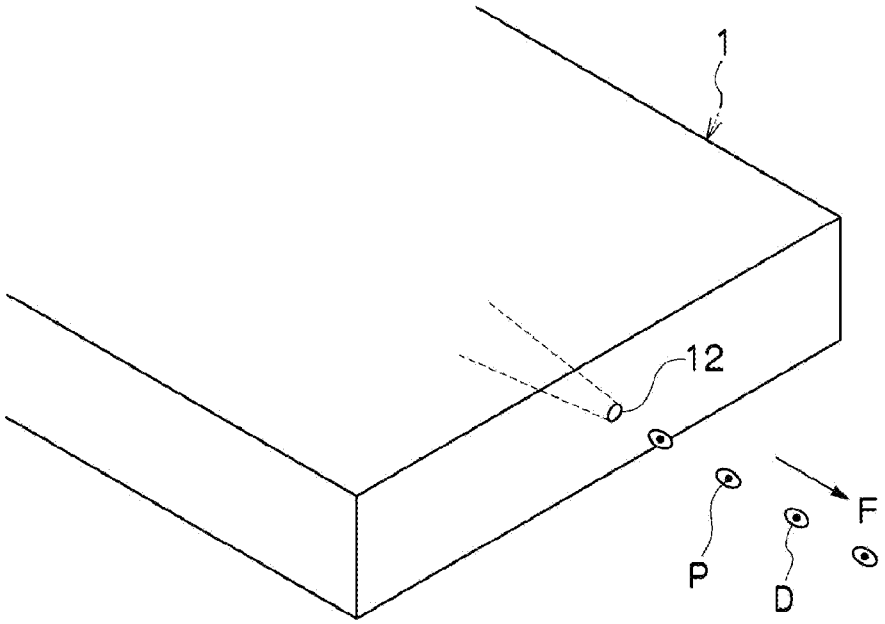
FIG. 6 A view schematically showing the sample liquid and the sheath liquid, which are transformed into liquid drops and discharged through the orifice 12.

FIG. 6 is a view schematically showing the sample liquid and the sheath liquid, which are transformed into liquid drops and discharged through the orifice 12. The sample-liquid laminar flow S containing the micro particles P is transformed into liquid drops through the orifice 12 together with the sheath-liquid laminar flow T and discharged as liquid drops D to the arrow F direction in the drawing.

The oscillating element 2 oscillates the microchip 1 at a predetermined frequency, to thereby transform the sample liquid and the sheath liquid into liquid drops in such a manner that each of the discharged liquid drop D contains each of the micro particles P as shown in the drawing. At this time, the frequency of the oscillating element 2 is set depending on a flowing speed (flow velocity) of the micro particles P and a liquid-delivering pressure to be detected by the optical detection means 3 at the light-irradiated portion 33, oscillating frequency of the microchip 1, and the like. Further, the frequency of the oscillating element 2 can be set also depending on the width and the depth of the flow path 11 at the location of the orifice 12 (that is, area of vertical cross-section).

4. Width and Depth of Flow Path at Each Location of Microchip

Figure 7C:
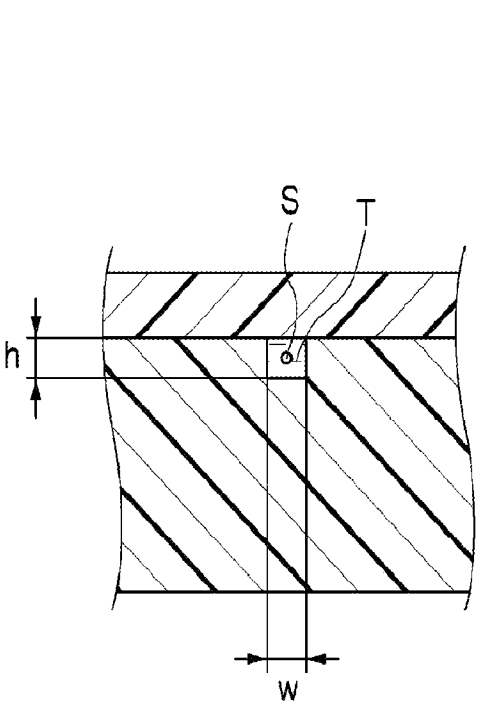
FIGS. 7A, 7B, and 7C Sectional schematic views describing the width and the depth of the flow path 11.
Figure 7B:
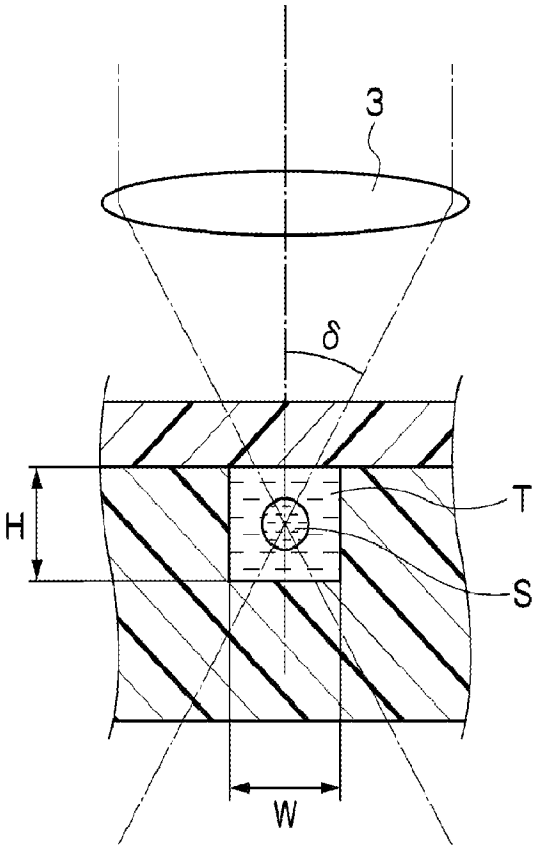
Figure 7A:
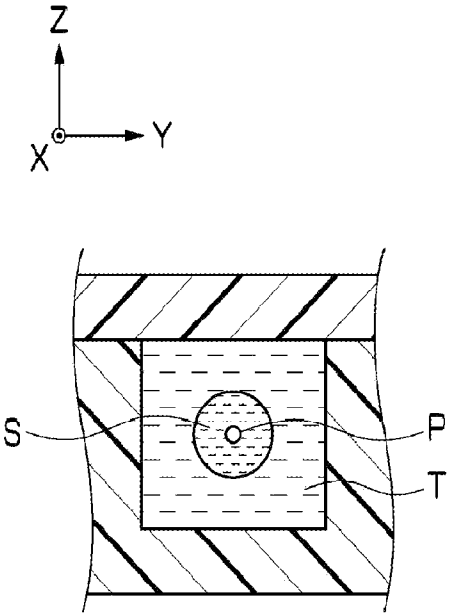

FIG. 7 are sectional schematic views describing the width and the depth at each location of the flow path 11. The drawing shows a YZ cross-section of the flow path 11. FIG. 7A shows the opening position of the micro tube 16, FIG. 7B shows the light-irradiated portion 33, and FIG. 7C shows the cross-section of the flow path 11 at the location of the orifice 12.

As shown in FIG. 7A, at the opening position of the micro tube 16, the sample-liquid laminar flow S and the sheath-liquid laminar flow T are delivered as the three-dimensional laminar flow in such a state that the sample-liquid laminar flow S is surrounded with the sheath-liquid laminar flow T. As previously mentioned, the width and the depth of the flow path 11 at the opening position of the micro tube 16 is appropriately set depending on the outer diameter of the micro tube 16 reflecting the diameter of each of the micro particles P, and, for example, is set to range from approximately 100 to 2000 μm.

The three-dimensional laminar flow formed through the micro tube 16 is delivered to the light-irradiated portion 33 in such a state that the width of the laminar flow is limited by the limiter portion 17 (see FIG. 7B). When the limiter portion 17 limits the width of the laminar flow, the three-dimensional laminar flow is delivered to the light-irradiated portion 33 in such a state that the micro particles P is arranged in line in the sample-liquid laminar flow S.

The laminar flow width of the sample-liquid laminar flow S and the sheath-liquid laminar flow T at the light-irradiated portion 33 can be arbitrarily set by appropriately adjusting the area of the cross-section of the limiter portion 17, the cross-section being perpendicular to the liquid-delivering direction.

Each of the width (W) and the depth (H) of the flow path 11 at the light-irradiated portion 33 is set to range from approximately 20 to 2000 μm in order to obtain a sufficiently large optically-detecting angle (numerical aperture of the optical system) of the optical detection means 3. In this manner, the optically detecting angle δ and the numerical aperture can be sufficiently increased.

In addition, the shape of the flow path 11 at the light-irradiated portion 33 is preferably rectangular with respect to a radiation direction of the measurement light of the optical detection means 3 through setting the width (W) to be larger than the depth (H). When the flow path 11 at the light-irradiated portion 33 is set to have such a wide shape, it is possible to increase the numerical aperture of the optical system.

The sample-liquid laminar flow S and the sheath-liquid laminar flow T passing through the light-irradiated portion 33 are delivered to the orifice 12 in such a state that the width of the laminar flow are again limited by the pressure-rising portion 13 as shown in FIG. 7C. When the pressure-rising portion 13 limits the width of the laminar flow, a discharging pressure of the sample liquid and the sheath liquid through the orifice 12 can be increased.

The laminar flow width of the sample-liquid laminar flow S and the sheath-liquid laminar flow T at the location of the orifice 12 can be arbitrarily set by appropriately adjusting the area of the cross-section of the pressure-rising portion 13, the cross-section being perpendicular to the liquid-delivering direction. At the orifice 12, in order to form the high frequency liquid drops at high speed, the width of the laminar flow of the sample-liquid laminar flow S and the sheath-liquid laminar flow T at the location of the orifice 12 is preferably set to be small so as to sufficiently increase the discharging pressure of the sample liquid and the sheath liquid. For this reason, the width (w) and the depth (h) of the flow path 11 at the opening of the orifice 12 are set to be smaller than the width (W) and the depth (H) at the light-irradiated portion 33. Otherwise, the cross-section area of the flow path 11 at the opening of the orifice 12 is set to be smaller than the cross-section area at the light-irradiated portion 33. Thus, it is preferred that each of the width (w) and the depth (h) of the flow path 11 at the opening of the orifice 12 be set to range from approximately 20 to 500 μm.

Figure 8:
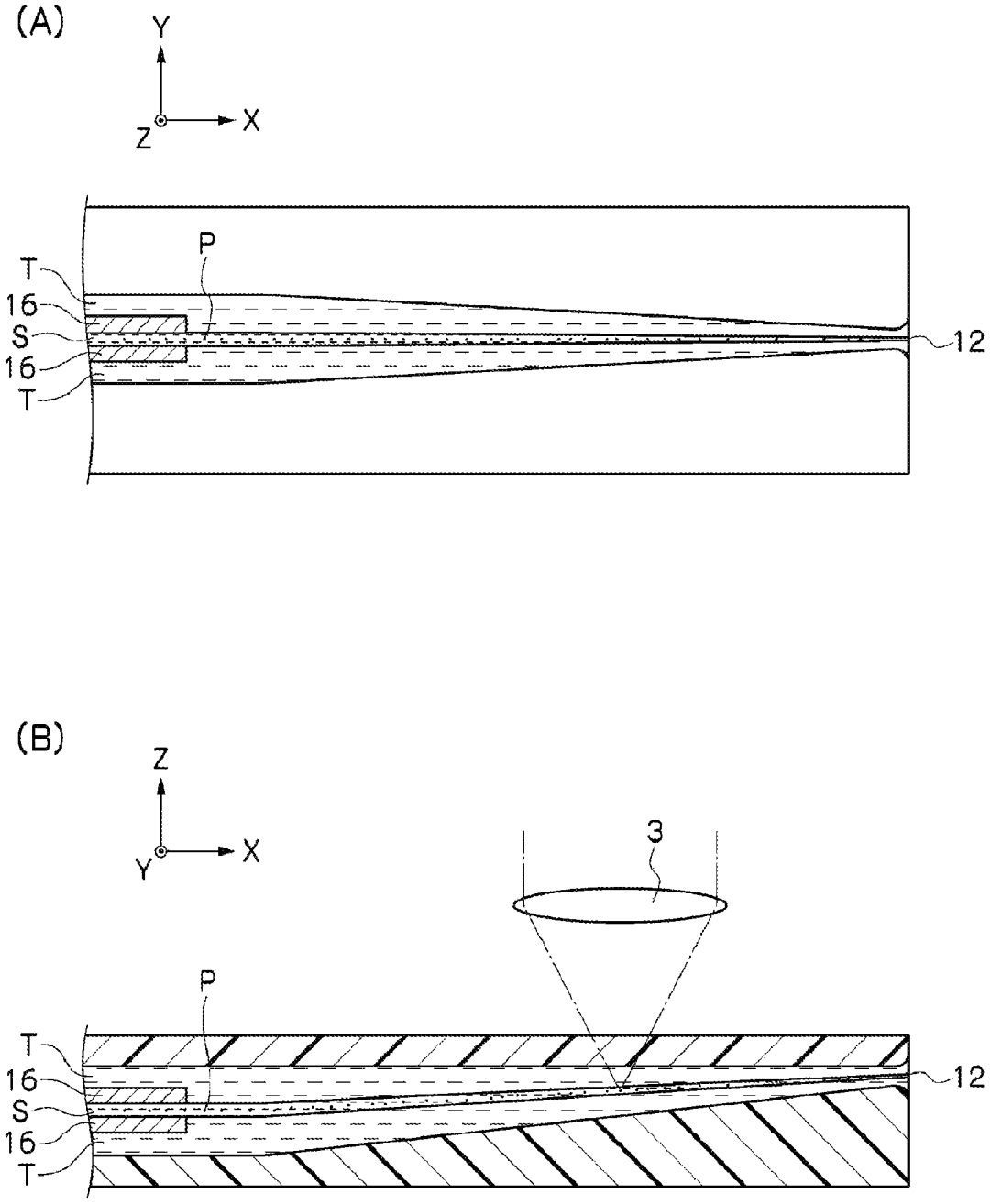
FIG. 8 Views describing another preferred embodiment with respect to the width and the depth of the flow path 11.

Here, the case of first setting, by the limiter portion 17, the width of the laminar flow of the three-dimensional laminar flow formed through the micro tube 16 to be a width suitable for optical detection of the micro particles at the light-irradiated portion 33, and then setting, by the pressure-rising portion 1, to a width with which the high-frequency liquid drop formation is enabled has been described. The limitation of the width of the laminar flow in the flow path 11 does not need to be performed in two phases of the limiter portion 17 and the pressure-rising portion 13, and, for example, as shown in FIG. 8, can be performed in such a manner that between the opening position of the micro tube 16 and the orifice 12 of the flow path 11, the width and the depth of the flow path or the cross-section area of the flow path become/becomes smaller continuously and gradually.

In addition to this, the shape of the flow path 11 can be set to be various shapes as long as the width and the depth of the flow path at the opening position of the micro tube 16, the light-irradiated portion 33, and the location of the orifice 12 fall within the above-mentioned suitable numeral range, or as long as the cross-section area of the flow path satisfies the above-mentioned magnitude relation.

Further, the shape of the opening of the orifice 12 can be an appropriate shape such as a square shape, a rectangular shape, or a circular shape. In addition, as shown in FIG. 8, an end surface portion of the opening portion can be also set to be an inverse-tapered shape. When the opening end surface portion of the orifice 12 is set to be such a trumpet shape, it is possible to achieve a smooth discharge of the formed liquid drops.

5. Operation of Micro-Particle Sorting Apparatus

Figure 9:
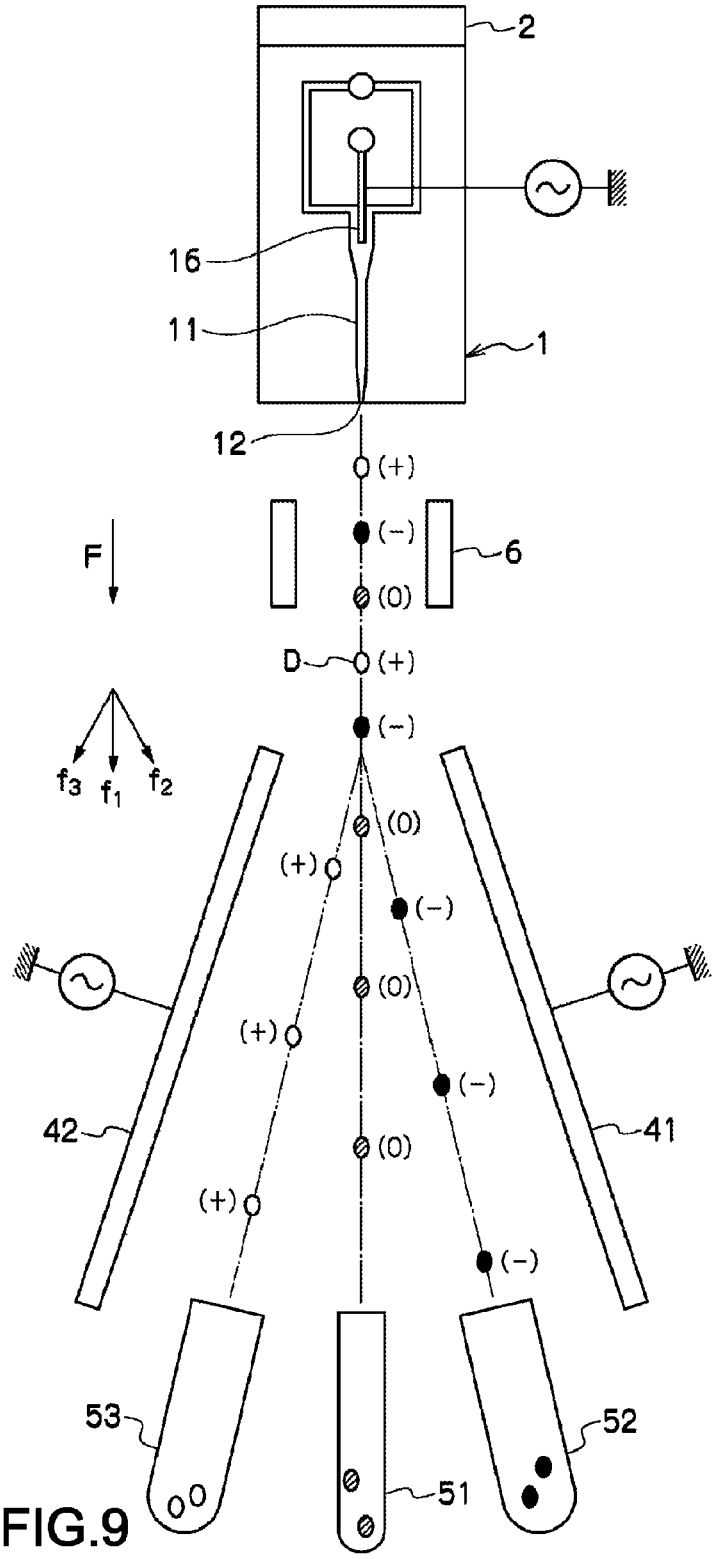
FIG. 9 A view schematically showing sorting of the micro particles by the micro-particle sorting apparatus A.

Next, the operation of the micro-particle sorting apparatus A will be described with reference to FIG. 9.

The sample liquid and the sheath liquid, which have passed through the light-irradiated portion of the flow path 11, are discharged through the orifice 12 into the space outside the chip. At the light-irradiated portion, the optical detection means detects the optical properties of the micro particles and at the same time detects the flowing speed (flow velocity) of the micro particles, intervals between the micro particles, and the like. The detected optical properties of the micro particles, the flow velocity, the intervals, and the like are converted into an electrical signal and output to a general control portion (not shown) of the apparatus. The general control portion controls, according to this signal, the oscillation frequency of the oscillating element 2. In this manner, the microchip 1 is oscillated so that each liquid drop D formed through the orifice 12 contains each of the micro particles P.

In addition, the general control portion controls voltage to be applied on the micro tube 16 in synchronous with the oscillating frequency of the oscillating element 2, to thereby switch the positive and negative of the electric charge to be added to the sheath liquid and the sample liquid, which flow through the flow path 11, and add the positive or negative charge to the liquid drop D formed through the orifice 12. The optical property of the micro particle, which has been detected by the optical detection means, is converted into an electrical signal and output to the general control portion. The general control portion controls, according to this signal, voltage to be applied on the micro tube 16, and determines the electric charge to be added to the liquid drop depending on the optical property of the micro particle contained in each liquid drop. Specifically, the general control portion positively charges, for example, the liquid drop containing the sorting-target micro particle having a predetermined property, while negatively charges the liquid drop containing no sorting-target micro particle.

At this time, in order to stabilize the charge state of the liquid drop D, in the micro-particle sorting apparatus A, in vicinity of the orifice 12, along the movement direction of the liquid drop discharged into the space outside the chip, grounding paired electrodes 6, 6 are arranged. The grounding electrodes 6, 6 are arranged so as to be opposed to each other while sandwiching the moving liquid drop therebetween, and is provided between the orifice 12 and paired electrodes 41, 42 for controlling the movement directions of the micro particles.

The movement direction of the liquid drop D charged and discharged through the orifice 12 is controlled due to the electrical force acting between the paired electrodes 41, 42. At this time, in order to precisely control the movement direction, it is necessary that a stable electric charge be added to the liquid drop in advance. On the paired electrodes 41, 42, significantly high voltage is applied, and hence high potential of the paired electrodes 41, 42 may influence the electric charge to be added at the orifice 12 through the micro tube 16 to the liquid drop D. In this case, there is a fear that the charge state of the liquid drop D lacks the stability. In view of this, in the micro-particle sorting apparatus A, the grounding electrodes 6, 6 are provided while being grounded between the orifice 12 and the paired electrodes 41, 42, to thereby eliminate such an influence due to the high potential of the paired electrodes 41, 42.

The control of the movement direction of the liquid drop D to be discharged through the orifice 12 is performed in the following manner, for example. That is, in the above-mentioned example of positively charging the liquid drop containing the sorting-target micro particle having a predetermined property, and negatively charging the liquid drop containing no sorting-target micro particle, by positively charging the paired electrode 41 and negatively charging the paired electrode 42, only the sorting-target micro particles can be sorted into the container 53. Specifically, regarding the liquid drop containing the sorting-target micro particle to which the positive electric charge has been added, the movement direction thereof is controlled to the arrow f3 direction and this liquid drop is guided into the container 53 due to electrical repelling force with respect to the paired electrode 41 and electrical attraction force with respect to the paired electrode 42. Meanwhile, regarding the liquid drop containing no sorting-target micro particle to which the negative electric charge has been added, the movement direction thereof is controlled to the arrow f2 direction and this liquid drop is guided into the container 52.

Alternately, for example, if no electric charge is added to the liquid drop containing the sorting-target micro particle having a predetermined property, and the liquid drop containing no sorting-target micro particle is positively or negatively charged, the paired electrodes 41, 42 are positively or negatively charged, only the sorting-target micro particles can be sorted into the container 51. In addition to this, the control of the movement direction of the liquid drop by using the electric charge to be added to the liquid drop D and the paired electrodes 41, 42 can be performed in various combinations similarly to the conventional flow cytometry. It should be noted that two or more containers for collecting the liquid drops D, and the number of containers is not limited to three. In addition, those containers may be configured as discharge channels that discharge the collected liquid drops without storing, or the collected micro particles not being as the sorting target may be set to be disposable.

Here, the case where with respect to the liquid drop D, the positive or negative charge is switched and added on the basis of the property of the micro particle contained in the liquid drop in order to perform sorting has been described as an example. The sorting of the liquid drops can be performed also by positively or negatively charging all liquid drops D, and switching voltage to be applied on the paired electrodes 41, 42 on the basis of the properties of the micro particles. Further, also in the case where the optical detection means is replaced by the electrical or magnetic detection means, by similarly controlling the movement directions of the liquid drops on the basis of the electrical or magnetic properties of the micro particles, the micro particles each having a predetermined property are collected into any one of the containers 51 to 53 for sorting.

As described above, the sorting of the micro particles by the micro-particle sorting apparatus A is characterized in that processes up to the property detection of the micro particles by the optical detection means 3 are performed in the microchip 1, and then, the control of the movement directions of the micro particles is performed as liquid drops discharged into the space outside the chip.

As previously mentioned, in the conventional flow cytometry using a flow cell, a flow cell part constituting a flow path system for forming a laminar flow and an orifice part for forming liquid drops are expensive, and the positions of them need to be finely adjusted (aligned) in order to prevent the laminar flow from being disturbed. Further, they are not configured to be disposable, and hence there is a fear that cross contamination between samples occur. In contrast, in the micro-particle sorting apparatus A, formation of the laminar flow and detection of the properties of the micro particles are performed in the microchip 1, in which the flow cell part and the orifice part are integrated, which enables a disposable use, and hence the cross contamination of the samples between measurements does not occur. In addition, the alignment as in the past becomes unnecessary, and hence it becomes possible for a user to more simply perform sorting.

Further, in the micro-particle sorting apparatus A, the control of the movement direction of the micro particle is performed in the space outside the chip, and hence, without need for performing the control of the movement directions of the micro particles in the flowing liquid as in the conventional flow cytometry applying the μ-TAS, a higher sorting speed can be obtained. In addition, in the micro-particle sorting apparatus A, it is possible to sufficiently increase the liquid-delivering pressure of the sample liquid and the sheath liquid in the flow path 11, and hence to discharge through the orifice 12 high frequency liquid drops at high speed. Thus, a high sorting speed can be obtained.

6. Cartridge

Figure 10:
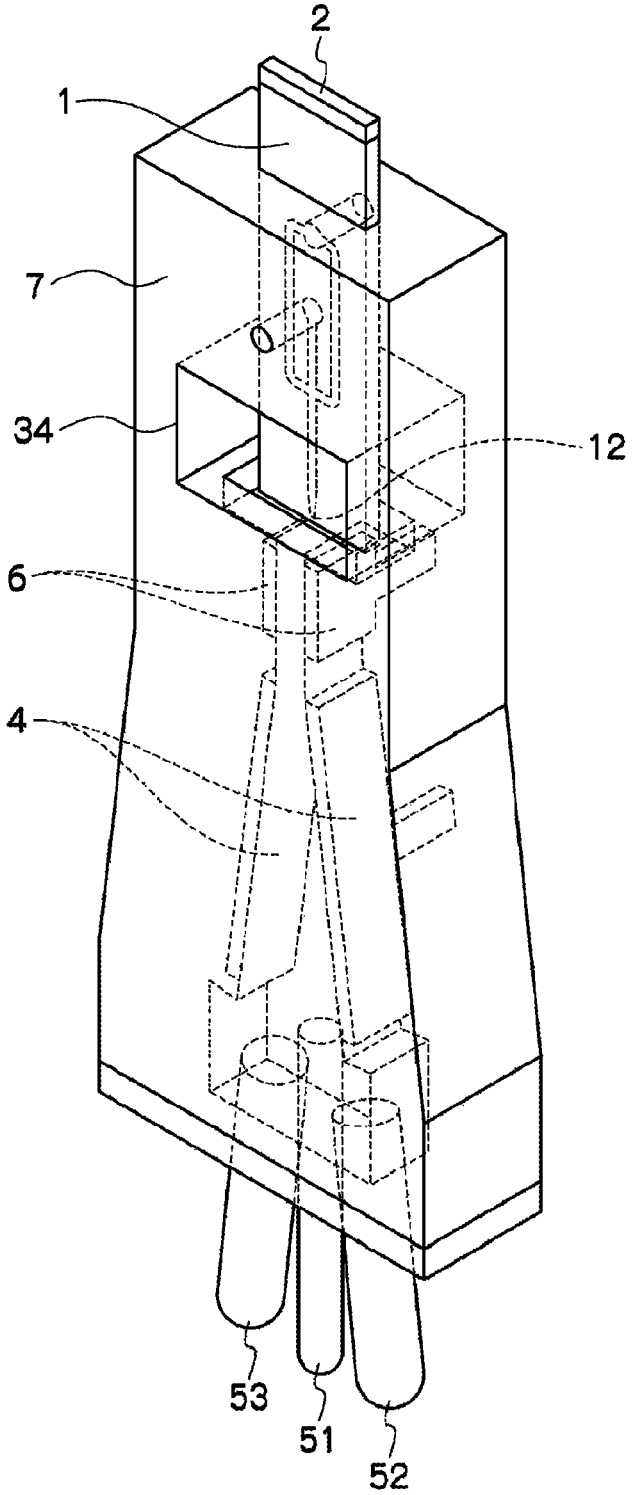
FIG. 10 A view describing a first embodiment of a cartridge according to the present invention.

In addition, in the micro-particle sorting apparatus A, it is preferred that the space in which the control of the movement direction of the liquid drop is performed be arranged in the cavity of the cartridge 7 (see FIG. 1) that can be hermetically sealed. That is, as shown in FIG. 10, at least the orifice 12 portion of the microchip 1 and the space in which the liquid drop D discharged through the orifice 12 to the outside of the chip moves are desirably arranged in an airtight space in the cartridge 7. At this time, in order to prevent formation of the liquid drop at the orifice 12 from being inhibited, the microchip 1 is attached to the cartridge 7 in such a state that the orifice 12 portion can oscillate at a predetermined oscillation frequency due to oscillation caused from the oscillating element 2. Specifically, it is desirable that an end side of the microchip 1 in opposite to the orifice 12 be fixed to the cartridge 7, and an orifice 12 end side of the microchip 1 be not in contact with the cartridge 7.

In the cavity of the cartridge 7, the paired electrodes 4, 4 for controlling the movement directions of the liquid drops and the grounding electrodes 6, 6 are provided. The containers 51 to 53 for collecting the liquid drops are detachably attached to the cartridge 7, and are set to communicate to the cavity of the cartridge 7 in an airtight manner during attachment.

As described above, the space between the orifice 12 through which the liquid drops are discharged and the containers 51 to 53 into which the liquid drops are collected is configured as the cartridge 7 cavity that can be hermetically sealed, and hence it is possible to prevent contamination materials such as micro liquid drops (aerosol) and the like generating when the liquid drops are formed through the orifice from being mixed into the sample. Further, at the same time, the liquid drops and the aerosol generating during formation of the liquid drops can be confined in the cartridge 7. Thus, in a case of sorting dangerous micro particles such as infectious cells, it is possible to prevent them from being exposed to the user and contaminating environment.

Figure 11:
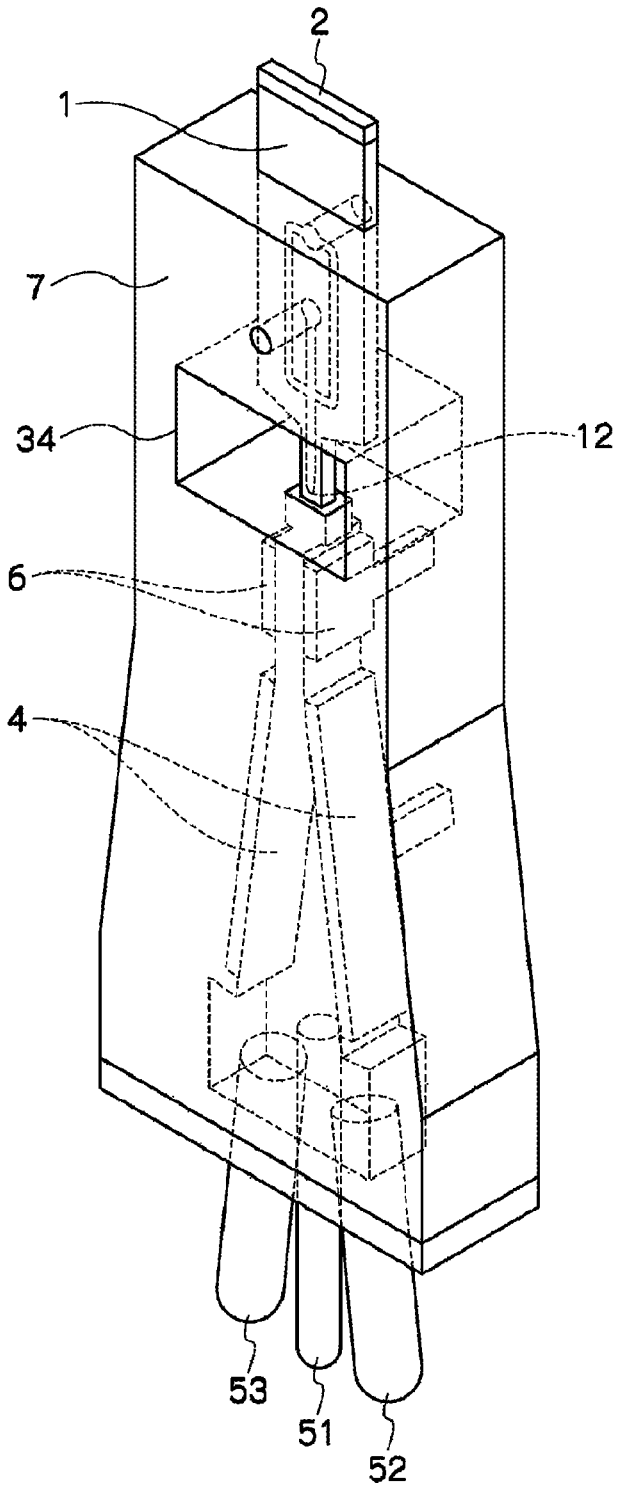
FIG. 11 A view describing a second embodiment of the cartridge according to the present invention.

Desirably, the cartridge 7 is generally formed of glass or various plastics similarly to the microchip 1, and has light transmittance for the measurement light from the optical detection means. Alternatively, as shown in the drawing, at a position of the microchip 1, which corresponds to the light-irradiated portion, an optical window 34 may be provided so that only this optical window 34 portion has transmittance for the measurement light. Otherwise, in a case of providing the optical window 34 by cutting out a part of the cartridge 7, even when objective lens having high numerical aperture and short motion distance is used as the optical detection means, the object lens can approach the light-irradiated portion surface of the microchip 1. In this case, desirably, in order to prevent contamination through the opened optical window, the orifice 12 end of the microchip 1 is formed to be slim, and as shown in FIG. 11, an opening being a communication hole between the microchip 1 and the space in which the movement direction of the liquid drop is to be controlled is set to be small. When the orifice 12 end of the microchip 1 is formed to be slim, it is possible to set the opening being the communication hole to be smaller than that in FIG. 10. In addition, when the orifice 12 end formed to be slim is inserted into the space in which the movement direction of the liquid drop is to be controlled, it is possible to increase a sealing efficiency for the liquid drops and the aerosol generating during formation of the liquid drops.

In order to further enhance air tightness in the cartridge 7, it is preferred that the optical window 34 be formed of a material having light transmittance, for example, glass. In this case, the optical window 34 is formed of, for example, a material having high transmittance, such as plastic having a surface on which an antireflective film or an antireflective nano structure or quartz. The thickness of the optical window is formed to be as small as possible, to thereby minimize optical loss.

Figure 12:
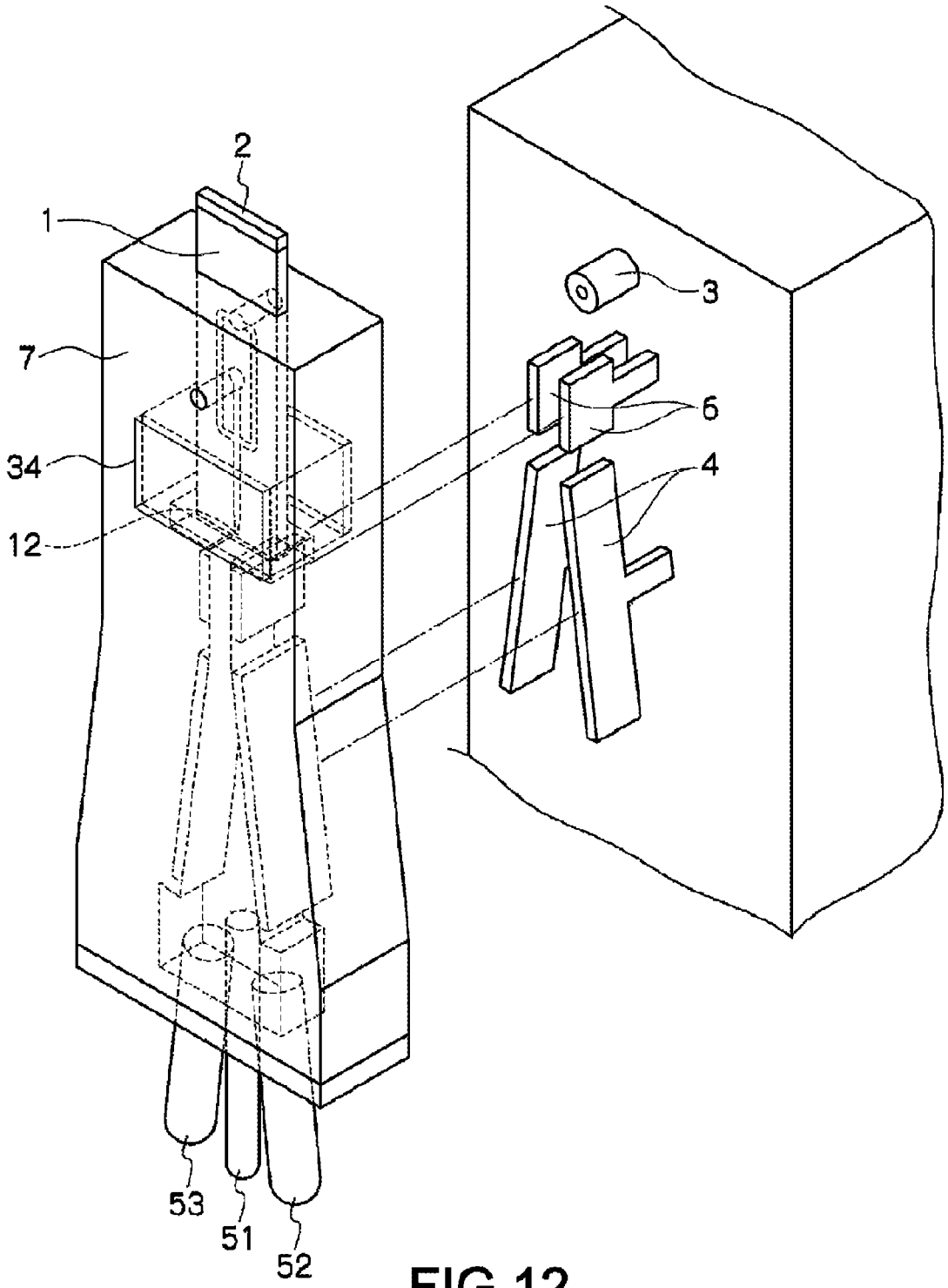
FIG. 12 A view describing a third embodiment of the cartridge according to the present invention.
Figure 13:
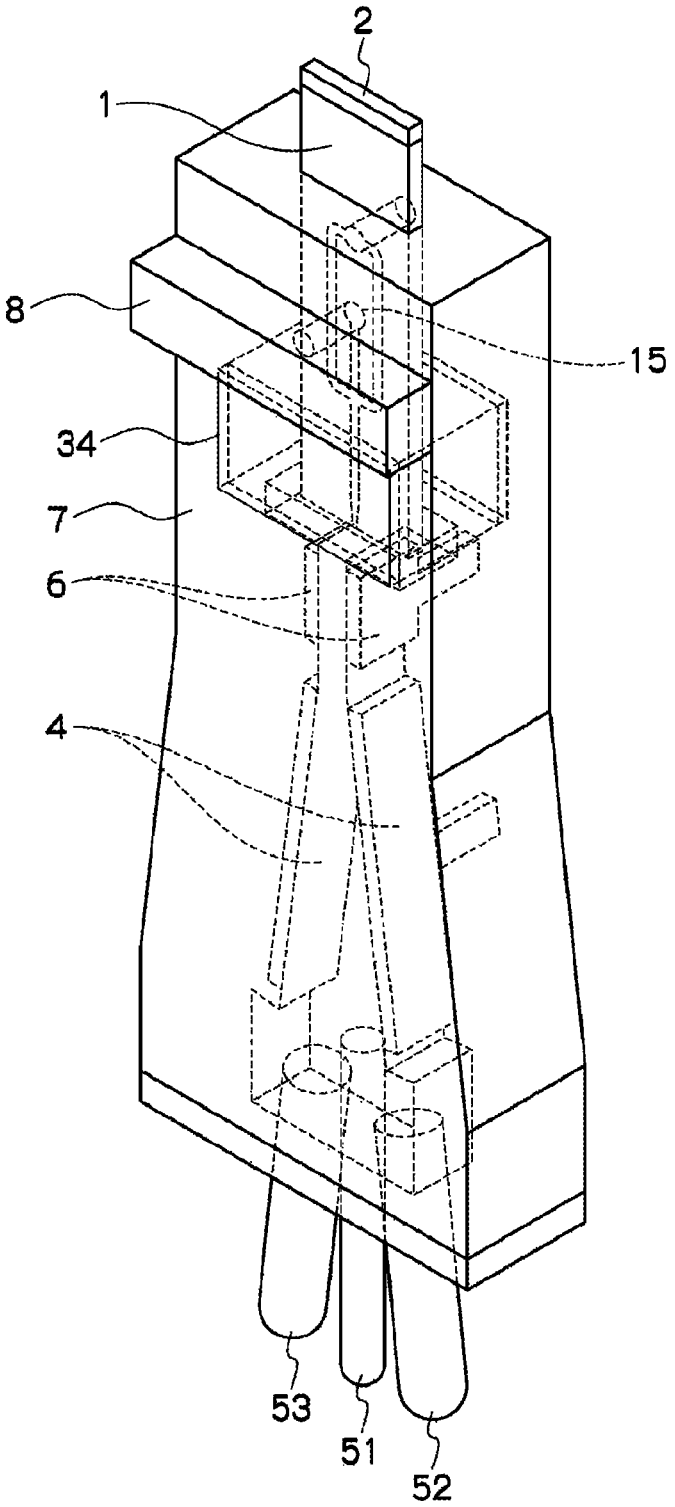
FIG. 13 A view describing a fourth embodiment of the cartridge according to the present invention.

FIG. 12 and FIG. 13 are views showing other preferred embodiments of the cartridge 7. As shown in FIG. 12, the paired electrodes 4, 4 that perform the control of the movement directions of the liquid drops and the grounding paired electrodes 6, 6 may be provided on the main body side of the micro-particle sorting apparatus A. In this case, fitting holes are formed in the cartridge 7, and thus, during attachment to the apparatus main body, the paired electrodes 4, 4 and the grounding paired electrodes 6, 6 can be inserted into the fitting holes. When inserted into the fitting holes, the paired electrodes 4, 4 and the grounding paired electrodes 6, 6 are arranged along the movement direction of the liquid drop discharged through the orifice of the microchip 1.

Further, as shown in FIG. 13, the cartridge 7 may be provided with a sample liquid reservoir 8 for supplying to the microchip 1 the sample liquid. The sample liquid from the sample liquid reservoir 8 is supplied through the sample liquid inlet 15 into the microchip 1. With this, also with respect to the supplying path for the sample liquid, the disposable use can be enabled. Thus, it is possible to further prevent the cross contamination of the samples between measurements.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF SYMBOLS

A micro-particle sorting apparatus
D liquid drop
P micro particles
S sample-liquid laminar flow
T sheath-liquid laminar flow
1 microchip
11 flow path
12 orifice
13 pressure-rising portion
14 sheath liquid inlet
15 sample liquid inlet
16 micro tube
17 limiter portion
2 oscillating element
3 optical detection means
33 light-irradiated portion
34 optical window
4, 41, 42 paired electrode
51, 52, 53 container
6 grounding electrode
7 cartridge
8 sample liquid reservoir The invention is claimed as follows:

[1. A microchip for analyzing a micro particle comprising:
a flow path through which a liquid containing a micro particle flows;

an orifice through which the liquid flowing through the flow path is configured to be discharged into a space outside the microchip; and a light-irradiated portion provided at a predetermined location of the flow path and configured to be irradiated with light, wherein a width of the flow path and a depth of the flow path within the microchip at the orifice are set to be smaller than a width of the flow path and a depth of the flow path within the microchip at the light-irradiated portion, and wherein the flow path is configured to gradually decrease within the microchip, from upstream of the orifice in a cross-section area perpendicular to a liquid-delivering direction between the light-irradiated portion and the orifice.]

[2. The microchip of claim 1, comprising an oscillating element for transforming the liquid into a liquid drop and discharging the liquid drop at the orifice.]

[3. The microchip of claim 1, comprising a micro tube that introduces, into a laminar flow of a liquid T flowing through the flow path, a laminar flow of a liquid S containing the micro particle, upstream of the liquid-delivering direction with respect to the light-irradiated portion.]

[4. The microchip of claim 3, wherein the micro tube includes a metal on which voltage can be applied.]

[5. The microchip of claim 1, wherein the microchip comprises a substrate and the flow path is provided within the substrate.]

[6. The microchip of claim 1, further comprising: a sheath liquid inlet, and wherein the sheath liquid inlet branches into a first direction and a second direction, and wherein the first direction is opposite to the second direction.]

7. A cartridge comprising:

[a microchip for analyzing a micro particle comprising:]

a flow path through which a liquid containing a micro particle flows;

an orifice through which the liquid flowing through the flow path is configured to be discharged into a space outside the [microchip] *flow path*; and a light-irradiated portion provided at a predetermined location of the flow path and configured to be irradiated with light; and a cavity in which at least the orifice and the space in which the liquid drop discharged outside through the orifice moves are configured, wherein a width of the flow path and a depth of the flow path at the orifice are set to be smaller than a width of the flow path and a depth of the flow path at the light-irradiated portion, wherein the flow path is configured to gradually decrease from upstream of the orifice in a cross-section area perpendicular to a liquid-delivering direction between the light-irradiated portion and the orifice, and wherein the cavity has *an optical window having* light transmittance for light transmitted to the light-irradiated portion.

8. The cartridge of claim 7, wherein the cavity is configured to be hermetically sealed.

9. The cartridge of claim 7, [wherein the microchip comprises] *further comprising* an oscillating element for transforming the liquid into a liquid drop and discharging the liquid drop at the orifice.

10. The cartridge of claim 7, [wherein the microchip comprises] *further comprising* a micro tube that introduces, into a [laminar] flow of a liquid T flowing through the flow path, a [laminar] flow of a liquid S containing the micro particle, upstream of the liquid-delivering direction with respect to the light-irradiated portion.

11. The cartridge of claim 10, [wherein the micro tube includes] *further comprising* a metal on which voltage is configured to be applied.

12. The cartridge of claim [7] *13*, wherein the [microchip] *micro fluidic structure* comprises a substrate and the flow path is provided within the substrate.

*13. The cartridge of claim 7, further comprising a micro fluidic structure comprising the flow path, the orifice, and the light irradiated portion.*

*14. The cartridge of claim 13, wherein the micro fluidic structure is a microchip.*

*15. The cartridge of claim 7, wherein the cartridge is detachably attached to a micro-particle sorting apparatus.*

*16. The cartridge of claim 7, wherein the cavity furtherly house a pair of electrodes opposed to each other while sandwiching the moving liquid drop along a movement direction of the liquid drop discharged into the space.*

*17. The cartridge of claim 7, wherein the space is an airtight space.*

*18. The cartridge of claim 7, wherein further comprising a container for receiving discharged liquid drop.*

*19. The cartridge of claim 18, wherein the container communicates with the cavity of the cartridge in an airtight manner.*

*20. The cartridge of claim 18, wherein the container is a plastic tube.*

*21. The cartridge of claim 18, wherein the container is detachably attached to the cartridge.*

*22. The cartridge of claim 7, wherein the optical window is a cut out part of the cartridge.*

*23. The cartridge of claim 7, wherein the optical window comprises plastic or glass or quartz.*

*24. The cartridge of claim 7, wherein the cartridge is connected to a sample supplying path.*

*25. The cartridge of claim 24, wherein the sample supplying path is disposable.*

*26. The cartridge of claim 7, wherein the cartridge comprises plastic or glass.*

*27. A micro-particle sorting apparatus comprising:*

*a light source configured to irradiate light to micro particles,*

*a flow path through which a liquid containing a micro particle flows;*

*an orifice through which the liquid flowing through the flow path is configured to be discharged into a space outside the flow path;*

*a light-irradiated portion provided at a predetermined location of the flow path and configured to be irradiated with light;*

*paired electrodes provided so as to be opposed to each other while sandwiching the moving liquid drop there between along a movement direction of the liquid drop discharged into the space outside the flow path; and*

*a cavity in which at least the orifice and the space in which the liquid drop discharged outside through the orifice moves are configured,*

*wherein a width of the flow path and a depth of the flow path at the orifice are set to be smaller than a width of the flow path and a depth of the flow path at the light-irradiated portion, wherein the flow path is configured to gradually decrease from upstream of the orifice in a cross-section area perpendicular to a liquid-delivering direction between the light-irradiated portion and the orifice, and*

*wherein the cavity has an optical window having light transmittance for light transmitted to the light-irradiated portion.*

*28. A micro particle sorting svstem of claim 27, comprising:*

*an optical detection means that detects an optical property of the micro particle flowing through the flow path, upstream of a liquid-delivering direction with respect to the orifice.*

*29. A micro particle sorting system of claim 27, wherein the light source is provided on a main body of a micro particle sorting apparatus.*

* * * * *